US012491363B2

(12) United States Patent
Chang et al.

(10) Patent No.: US 12,491,363 B2
(45) Date of Patent: Dec. 9, 2025

(54) ELECTRICAL STIMULATION SYSTEM AND A METHOD THEREOF

(71) Applicant: Taiwan Resonant Waves Research Corp., Taipei (TW)

(72) Inventors: Wen-Chieh Chang, Taipei (TW); Lee-Ming Chuang, Taipei (TW)

(73) Assignee: TAIWAN RESONANT WAVES RESEARCH CORP., Taipei (TW)

( * ) Notice: Subject to any disclaimer, the term of this patent is extended or adjusted under 35 U.S.C. 154(b) by 356 days.

(21) Appl. No.: 18/189,496

(22) Filed: Mar. 24, 2023

(65) Prior Publication Data

US 2024/0316344 A1 Sep. 26, 2024

(51) Int. Cl.
*A61N 1/36* (2006.01)
*A61N 1/04* (2006.01)

(52) U.S. Cl.
CPC ....... *A61N 1/36034* (2017.08); *A61N 1/0492* (2013.01)

(58) Field of Classification Search
CPC .......................... A61N 1/36034; A61N 1/0492
USPC .......................................................... 607/59
See application file for complete search history.

(56) References Cited

U.S. PATENT DOCUMENTS 3,911,930 A 10/1975 Hagfors et al.
2007/0156182 A1* 7/2007 Castel ................ A61N 1/36034 607/2
2016/0121113 A1 5/2016 Chang et al.
2016/0243354 A9 8/2016 Palermo et al.
2017/0246458 A1 8/2017 Li et al.
2019/0224481 A1 7/2019 Wingeier
2022/0054864 A1 2/2022 Bandoni

FOREIGN PATENT DOCUMENTS

AU 2017202546 B2 1/2019
CN 102905760 A 1/2013
CN 105263571 A 1/2016
CN 108463163 B 1/2022
JP 2017196397 A 11/2017
WO WO2013074809 A1 5/2013
WO WO2018125538 A1 7/2018
WO WO2020236946 A1 11/2020

OTHER PUBLICATIONS

Office Action (with Search Report) issued in corresponding TW application No. 11221081920 dated Oct. 31, 2023 (4 pages).
Jin-Ying Lu et al; "A Randomized Trial on the Effect of Transcutaneous Electrical Nerve Stimulator on Glycemic Control in Patients with Type 2 Diabetes"; Mar. 25, 2022; Journal: Research Square; pp. 1-21.
Lu et al., "A randomized trial on the effect of transcutaneous electrical nerve stimulator on glycemic control in patients with type 2 diabetes." Scientific Reports 13 (Feb. 15, 2023): 10 pages.

* cited by examiner

*Primary Examiner* — Nadia A Mahmood
(74) *Attorney, Agent, or Firm* — MUNCY, GEISSLER, OLDS & LOWE, P.C.

(57) ABSTRACT

The present invention relates to an electrical stimulation system and a method thereof. The electrical stimulation system includes an electrical stimulation generator and at least one electrode structure. The electrical stimulation generator is used to generate an electric pulse combination which is transmitted to the skin of an individual through the electrode structure for stabilizing blood glucose fluctuations and reducing inflammation.

8 Claims, 6 Drawing Sheets

ELECTRICAL STIMULATION SYSTEM AND A METHOD THEREOF

BACKGROUND OF THE INVENTION

1. Field of the Invention

The present invention relates to an electrical stimulation system and a method thereof, particularly a system and method for generating electrical pulse combinations and delivering the electrical pulse combinations to the skin of a diabetic patient for stabilizing blood glucose fluctuations or reducing inflammation.

2. Description of Related Art

Type 2 diabetes is a chronic metabolic disease, causing hyperglycemia due to relative insulin deficiency, and insulin resistance. No cure for type 2 diabetes has yet been developed. Drug therapy is still the most common way to reduce hyperglycemia and diabetes complications. However, taking oral antidiabetic drugs such as biguanides, sulfonylureas, meglitinides, inhibitors or GLP-1 analogs may cause discomfort to patients (such as hypoglycemia) due to drug side effects, which may result in decreased quality of life and reluctance of patients to take their medications on time. Therefore, there is an urgent need for a non-drug technique that can assist or replace current treatments.

Furthermore, there are currently few relevant data on the application of Transcutaneous Electrical Nerve Stimulator (TENS) to the human body to treat or improve diabetic diseases. Only a few documents in the prior art disclosed that the use of electrical stimulation devices can reduce the glycated hemoglobin (HbA1c) and fasting plasma glucose levels in diabetes-induced model mice, but there is no such effect as effectively stabilizing blood glucose fluctuations and reducing related inflammation in humans.

Accordingly, to solve the problem that the prior art and the conventional electrical stimulation device cannot be effectively applied to the human body to treat type 2 diabetes and etc., the present invention provides an electrical stimulation system that can generate electric pulse combinations and transmit electric pulse combinations to the skin of individuals through the electrode structure. Above all, it can effectively stabilize blood glucose fluctuations in diabetic patients and reduce the expression of inflammatory factors in their bodies.

SUMMARY OF THE INVENTION

The present invention is to provide an electrical stimulation system and a method for generating electric pulse combinations, whereby the generated electric pulse combination can improve diabetes-related diseases. Moreover, the electrical stimulation system of the present invention generates an electric pulse combination, which is transmitted to the body through the electrode structure attached to the skin of human body. The electrical stimulation system of the present invention is a non-invasive and portable electrical stimulation system that not only has no risk of side effects but is also more suitable than current diabetes medications when used on the human body. Therefore, the electric pulse combinations generated by the electrical stimulation system is capable of stabilizing blood glucose fluctuations and reducing inflammation in diabetic patients.

To achieve the purpose described above, the present invention provides an electrical stimulation system including an electrical stimulation generator and at least one electrode structure. The electrical stimulation generator is to generate an electric pulse combination, wherein a frequency of the electric pulse combination ranging from 1 to 20,000 Hz, and comprises a first frequency group, a second frequency group, and a third frequency group, wherein the first frequency group, the second frequency group, and the third frequency group are respectively composed of multiple single-phase pulse groups, wherein each single-phase pulse group has a duty cycle greater than or equal to 50% and a waveform that is a square wave. The electrode structure is electrically connected to the electrical stimulation generator and having a contact surface applied to the skin of an individual to deliver the electric pulse combination; wherein the electric pulse combination is outputted in sequence from the first frequency group to the third frequency group, wherein the first frequency group ranges from 10 to 20,000 Hz, the second frequency group ranges from 1 to 30 Hz, and the third frequency group ranges from 5 to 30 Hz.

In one embodiment, the output time of the first frequency group is between 2300 and 2350 seconds, the output time of the second frequency group is between 900 and 1000 seconds, and the output time of the third frequency group is between 320 and 400 seconds.

In one embodiment, the output time of the electric pulse combination is between 3520 and 3750 seconds.

In one embodiment, the electric pulse combination has a potential difference, which is less than 10 Vpp.

In one embodiment, the electrode structure contacts the abdominal skin of the individual.

In one embodiment, the electrical stimulation system is capable of improving symptoms of diabetes, which includes stabilizing blood glucose fluctuations or reducing inflammation.

In one embodiment, stabilizing blood glucose fluctuations refers to reducing glycemic variability (GV).

In one embodiment, reducing inflammation refers to decreasing the protein expression of C-reactive protein (CRP) and fibroblast growth factor 21 (FGF-21), which also has the potential to reduce fibrosis.

The present invention further provides a method for generating an electric pulse combination in the electrical stimulation system, and the electric pulse combination generated by the method will be delivered to a diabetic patient through an electrode structure. By transdermally delivering a single-phase pulse combination generated by this method to an individual, it can effectively reduce the expression of inflammatory factors and stabilize blood glucose fluctuation in the body of diabetic patients, which shows better efficacy than the prior art.

To achieve the purpose described above, the present invention provides an electrical stimulation system and a method that generates the electric pulse combination.

After referring to the drawings and the implementation methods described later, those with ordinary knowledge in this field can understand other objectives of the present invention, as well as the technical means and implementation modes of the present invention.

DETAILED DESCRIPTION OF THE PREFERRED EMBODIMENT

Figure 1:
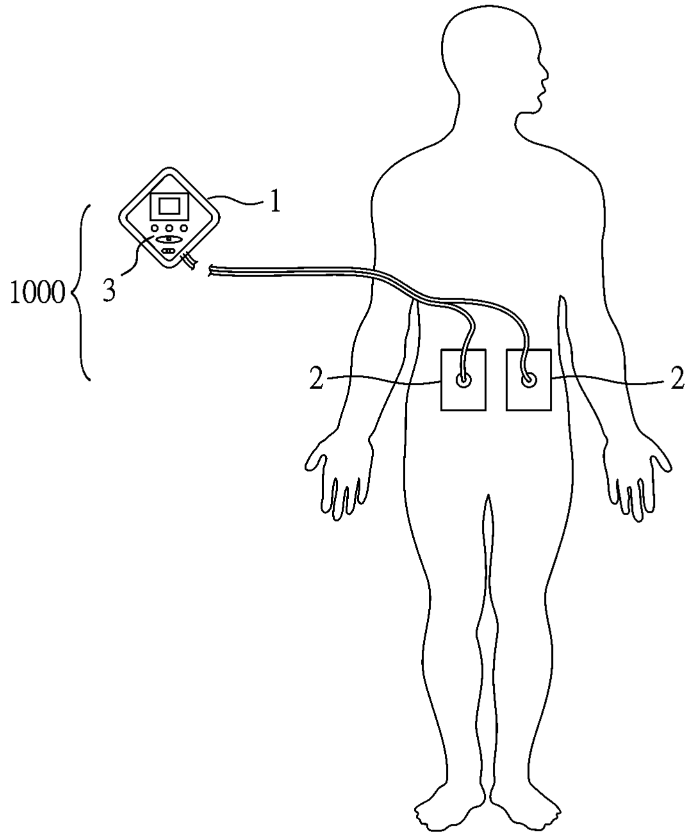
FIG. 1 is a schematic view of the electrical stimulation system of the present invention.

Reference will now be made in detail to the embodiments of the present invention, examples of which are illustrated in the accompanying drawings, and are not intended to limit the present invention, applications, or implementations described in these embodiments. Wherever possible, the same reference numbers are used in the drawings and the description to refer to the same or like parts. It should be noticed that, in the following embodiments and the attached drawings, elements unrelated to the present invention are omitted from the depiction; and dimensional relationships among individual elements in the drawings are provided only for ease of understanding, but not to limit the actual scale.

Please refer to FIG. 1, which is a specific schematic diagram of an electrical stimulation system 1000 according to one embodiment of the present invention. The electrical stimulation system 1000 includes an electrical stimulation generator 1 and two electrode structures 2. The electrical stimulation generator 1 can be connected to the electrode structures 2 through a signal transmission line. The electrode structures 2 are attached to an individual's abdomen and can deliver an electric pulse combination generated by the electrical stimulation generator 1 to the individual. It should be noted that the use of the signal transmission line and the corresponding electrode structures 2 in the electrical stimulation system 1000 in this embodiment is an illustration, which can be adjusted according to the usage scenario or requirement and is not limited to this embodiment.

In this embodiment, the electrical stimulation system 1000 can include an interface module 3. The main function of the interface module 3, which is not particularly limited in the present invention, is to allow users to operate and adjust the electrical stimulation system 1000. The interface module 3 includes the system operation switch and the command signal for the default program execution, and to display the operation information for users.

The electrical stimulation generator 1 is used to generate an electric pulse combination, and the electrical stimulation pulse combination includes a first frequency group, a second frequency group, and a third frequency group. The first frequency group, the second frequency group, and the third frequency group are respectively composed of a plurality of single-phase pulse groups, the single-phase pulse group has a duty cycle greater than or equal to 50%, and a waveform as a square wave.

The electrical stimulation generator 1 can include a control module, a driving module, and an output module (not shown in the figure), the combination of the aforementioned modules can trigger and receive the command signal generated by the interface module 3 and then can output the corresponding driving signal to adjust and output the preset electric pulse with relevant duty cycle, frequency and potential difference in the program. It should be noted that the combination of the control module, the driving module, and the output module can be adjusted according to actual needs, which is not limited to the present invention.

In this embodiment, the electrode structures 2 are sheet-like, cloth-like or wearable device structure, which can be pasted or contact the individual, and the electrode structures 2 are electrically connected to the electrical stimulation generator 1 for delivering the electric pulse combination generated by the electrical stimulation generator 1 to the individual, the structure of which is not limited in the present invention. In detail, the electrode structures 2 have a contact surface, and the contact surface contacts the skin of the user, and the contact position of the user in the embodiment of the present invention is preferably the abdominal skin.

Figure 6:
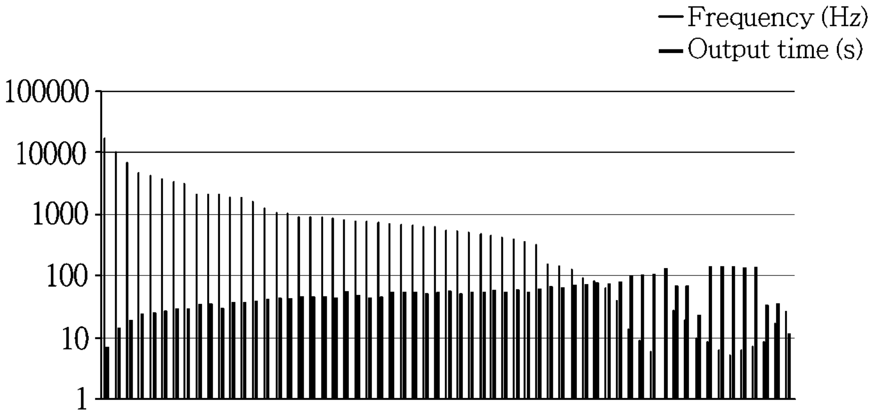
FIG. 6 is a plot of the electric pulse combination of one embodiment of the present invention.

Next, the frequency of the electric pulse combination will be described. Please refer to FIG. 6, the electric pulse combination is outputted sequentially from the first frequency group to the third frequency group, the range of the first frequency group is preferably 10 to 20000 Hz, more preferably 13 to 18122 Hz, and the range of the second frequency group is preferably 1 to 30 Hz, more preferably 1 to 28 Hz, and the range of the third frequency group is preferably 5 to 30 Hz, more preferably 6 to 26 Hz. Wherein, the output time of the electric pulse combination is preferably between 3520 to 3750 seconds, more preferably 3633 seconds. The first frequency group has an output time preferably between 2300 to 2350 seconds, more preferably 2312 seconds; the second frequency group has an output time preferably between 900 to 1000 seconds, more preferably 949 seconds; and the third frequency group has an output time preferably between 320 to 400 seconds, more preferably 372 seconds. The output frequency and output time of the frequency range in the first frequency group, the second frequency group, and the third frequency group can be adjusted according to actual needs without no limitation.

Particularly, in this embodiment, the first frequency group is composed of 47 single-phase pulse groups, which sequentially includes the first single-phase pulse group of 18122 Hz and output time of 7 seconds; the second single-phase pulse group of 10000 Hz and output time of 15 seconds; the third single-phase pulse group of 7344 Hz and output time of 19 seconds; the fourth single-phase pulse group of 5000 Hz and output time of 24 seconds; the fifth single-phase pulse group of 4200 Hz and output time of 26 seconds; sixth single-phase pulse group of 3672 Hz and output time of 28 seconds; seventh single-phase pulse group of 3175 Hz and output time of 30 seconds; eighth single-phase pulse group of 3000 Hz and output time of 31 seconds; the ninth single-phase pulse group of 2127 Hz and output time of 36 seconds; the tenth single-phase pulse group of 2112 Hz and output time of 35 seconds; the eleventh single-phase pulse group of 2007 Hz and output time of 30 seconds; the twelfth single-phase pulse group of 1865 Hz and output time of 37 seconds; the thirteenth single-phase pulse group of 1850 Hz and output time of 37 seconds; the fourteenth single-phase pulse group of 1550 Hz and output time of 39 seconds; the fifteenth single-phase pulse group of 1234 Hz and output time of 42 seconds; the sixteenth single-phase pulse group of 1043 Hz and output time of 44 seconds; the seventeenth single-phase pulse group of 1000 Hz and output time of 45 seconds; the eighteenth single-phase pulse group of 921 Hz and output time of 45 seconds; the nineteenth single-phase pulse group of 880 Hz and output time of 47 seconds; the twentieth single-phase pulse group of 867 Hz and output time of 46 seconds; the twenty-first single-phase pulse group of 807 Hz and output time of 45 seconds; the twenty-second single-phase pulse group of 778 Hz and output time of 57 seconds; the twenty-third single-phase pulse group of 751 Hz and output time of 49 seconds; the twenty-fourth single-phase pulse group of 730 Hz and output time of 45 seconds; the twenty-fifth single-phase pulse group of 705 Hz and output time of 48 seconds; the twenty-sixth single-phase pulse group of 668 Hz and output time of 54 seconds; the seventh single-phase pulse group of 652 Hz and output time of 55 seconds; the twenty-eighth single-phase pulse group of 625 Hz and output time of 54 seconds; the twenty-ninth single-phase pulse group of 612 Hz and output time of 51 seconds; the thirtieth single-phase pulse group of 595 Hz and output time of 54 seconds; the thirty-first single-phase pulse group of 542 Hz and output time of 57 seconds; the thirty-second single-phase pulse group of 522 Hz and output time of 53 seconds; the thirty-third single-phase pulse group of 484 Hz and output time of 55 seconds; the thirty-fourth single-phase pulse group of 462 Hz and output time of 56 seconds; the thirty-fifth single-phase pulse group of 435 Hz and output time of 60 seconds; the thirty-sixth single-phase pulse group of 421 Hz and output time of 56 seconds; the thirty-seventh single-phase pulse group of 380 Hz and output time of 60 seconds; the thirty-eighth single-phase pulse group of 348 Hz and output time of 55 seconds; the thirty-ninth single-phase pulse group of 302 Hz and output time of 60 seconds; the fortieth single-phase pulse group of 160 Hz and output time of 69 seconds; the forty-first single-phase pulse group 141 Hz and output time of 65 seconds; the forty-second single-phase pulse group of 125 Hz and output time 72 of seconds; the forty-third single-phase pulse group of 95 Hz and output time 76 of seconds; the forty-fourth single-phase pulse group of 80 Hz and output time of 78 seconds; the forty-fifth single-phase pulse group of 66 Hz and output time of 75 seconds; the forty-sixth single-phase pulse group of 40 Hz and output time of 85 seconds; and the forty-seventh single-phase pulse group of 13 Hz and output time of 105 seconds. Furthermore, the second frequency group consists of 9 single-phase pulse groups, which sequentially includes the forty-eighth single-phase pulse group of 9 Hz and output time of 106 seconds; the forty-ninth single-phase pulse group of 6 Hz and output time of 110 seconds; the fiftieth single-phase pulse group of 1 Hz and output time of 133 seconds; the fifty-first single-phase pulse group of 28 Hz and output time of 72 seconds; the fifty-second single-phase pulse group of 19 Hz and output time of 72 seconds; the fifty-third single-phase pulse group of 10 Hz and output time of 24 seconds; the fifty-fourth single-phase pulse group of 8 Hz and output time of 144 seconds; the fifty-fifth single-phase pulse group of 6 Hz and output time of 144 seconds; and the fifty-sixth single-phase pulse group of 5 Hz and output time of 144 seconds. Finally, the third frequency group consists of 5 single-phase pulse groups, which sequentially includes the fifty-seventh single-phase pulse group of 6 Hz and output time of 144 seconds; the fifty-eighth single-phase pulse group of 7 Hz and output time of 144 seconds; the fifty-ninth single-phase pulse group of 8 Hz and output time of 36 seconds; the sixtieth single-phase pulse group of 17 Hz and output time of 36 seconds; and the sixty-first single-phase pulse group of 26 Hz and output time of 12 seconds.

In this embodiment, the single-phase pulse groups in the first frequency group are outputted sequentially, and when the previous frequency ends, the next frequency will be lower than the previous frequency. However, the second frequency group may include a first frequency variation group and a second frequency variation group, wherein the number of the single-phase pulse groups in the first frequency variation group is less than the number in the second frequency variation group. Specifically, the range of the first frequency variation group is preferably 10 to 1 Hz, more preferably 9 to 1 Hz, and has an output time preferably between 300 to 360 seconds, more preferably 349 seconds. The range of the second frequency variation group is preferably 30 to 4 Hz, more preferably 28 to 5 Hz, and has an output time preferably between 550 to 650 seconds, more preferably 600 seconds.

Continuing from the above, the first frequency variation group sequentially outputs the forty-eighth single-phase pulse group of 9 Hz, the forty-ninth single-phase pulse group of 6 Hz and the fiftieth single-phase pulse group of 1 Hz. Wherein when the previous frequency ends, the next frequency will be lower than the previous frequency; the second frequency variation group outputs sequentially the fifty-first single-phase pulse group of 28 Hz, the fifty-second single-phase pulse group of 19 Hz, The fifty-third single-phase pulse group of 10 Hz, the fifty-fourth single-phase pulse group of 8 Hz, the fifty-fifth single-phase pulse group of 6 Hz, and the fifty-sixth single-phase pulse group of 5 Hz. Wherein when the previous frequency ends, the next frequency will be lower than the previous frequency. Then, in this embodiment, the single-phase pulse groups in the third frequency group is outputted sequentially, and when the previous frequency ends, the next frequency will be higher than the previous frequency.

Specifically, the range of the potential difference generated by the electric pulse combination is less than 10 Vpp, wherein the potential difference used in the present invention is a voltage potential difference, and similarly, the potential difference used in the present invention can be common in the technical field including peak-to-peak voltage (Vpp), maximum voltage (Vmax) or root mean square voltage (Vrms). The range of the potential difference is preferably less than or equal to 7.2 Vpp. The electric stimulation system 1000 of the present invention can stably output the voltage potential difference within the aforementioned range and provide the user with a range of voltage potential differences suitable for the human body.

In this embodiment, the electrical stimulation system 1000 can be used to improve symptoms of diabetes, which include stabilizing blood glucose fluctuations or reducing inflammation.

In this embodiment, the electrical stimulation system 1000 can be used for diabetic patients to stabilize blood glucose fluctuations, wherein stabilizing blood glucose fluctuations is to reduce glycemic variability (GV).

In this embodiment, the electrical stimulation system 1000 can be used for diabetic patients to reduce inflammation, wherein reducing inflammation is to reduce the protein expression of C-reactive protein (CRP) and fibroblast growth factor 21 (FGF-21), which also has the potential to reduce fibrosis.

In this embodiment, there is also a method using the above-mentioned electrical stimulation system for diabetic patients, the method includes generating an electric pulse combination that can stabilize blood glucose fluctuations and reduce inflammation.

Embodiment 1

[Stabilizing Blood Glucose Fluctuations]

To verify the feasibility of the present invention, the human experiment design of improving diabetes-related diseases was performed first. This experiment was a multi-center, prospective, double-blind, randomized, placebo-controlled trial (clinical trial number: NCT03102424), in which patients with type 2 diabetes were given the electrical stimulation system of the present invention (with electric pulse combination shown in FIG. 6) to improve blood glucose control of the patients. The type 2 diabetic patients who met all the inclusion criteria and did not meet the exclusion criteria were enrolled as subjects and randomly divided into a group using the electrical stimulation system of the present invention (hereinafter referred to as the TENS group) and a placebo group in a ratio of 1:1, wherein the subjects of the placebo group were given ineffective electrical stimulation. The method was to attach the electrode structures of the electrical stimulation system of the present invention to the left and right sides of the subject's abdominal skin respectively one hour after dinner, one hour a day and at least five-days a week for twenty weeks. The subjects checked their blood glucose 7 times a day (before and 2 hours after each meal and at bedtime) on week 0, 4, 12, and 20 as self-monitoring of blood glucose (SMBG).

The test results of the electrical stimulation system of this embodiment are shown in Table 1.

TABLE 1

| | Baseline (Week 0) | | Week 20 | |
|---|---|---|---|---|
| | TENS | Placebo | TENS | Placebo |
| HbA1c, % | 8.1 | 8.1 | 7.9 | 7.8 |
| Mean 7-point SMBG | 184 | 180 | 173 | 172 |
| MAGE, mg/dL | 85 | 88 | 66 | 79 |
| CRP, mg/dL | 0.22 | 0.24 | 0.16 | 0.38 |
| FGF-21, mg/dL | 0.29 | 0.35 | 0.24 | 0.32 |

Figure 2:
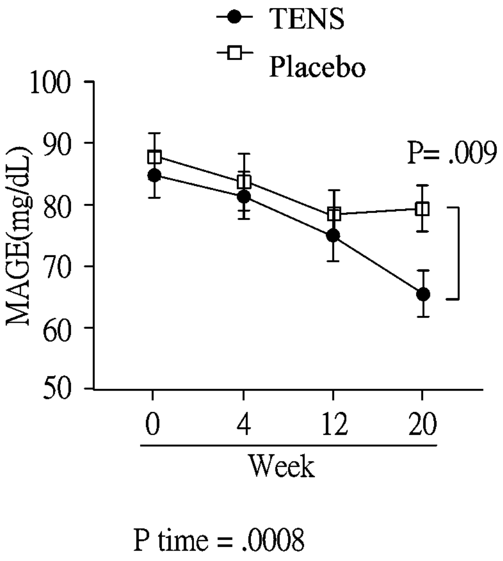
FIG. 2 is a graph of the mean amplitude of glycemic excursion (MAGE) of diabetic patients after using the electrical stimulation system in one embodiment of the present invention.

In detail, in the embodiment of the present invention, the mean amplitude of glycemic excursion (MAGE) was calculated using 7-point SMBG data, which is an index representing glycemic variability (GV). As shown in FIG. 2 and Table 1, the results showed that after 20 weeks of electrical stimulation treatment, the 7-point SMBG of the TENS group dropped from 184 at the baseline to 173, and that of the placebo group dropped from 180 at the baseline to 172; and after calculation, the MAGE of the TENS group decreased from 85 at the baseline to 66, while that of the placebo group decreased from 88 at the baseline to 79. It can be realized that in the TENS group, from week 0 to week 20, the changes of 7-point SMBG and MAGE showed a downward trend, and the change of MAGE was statistically significant (P=0.009). Compared with the placebo group, it could maintain a relatively more stable blood glucose variability.

Figure 3:
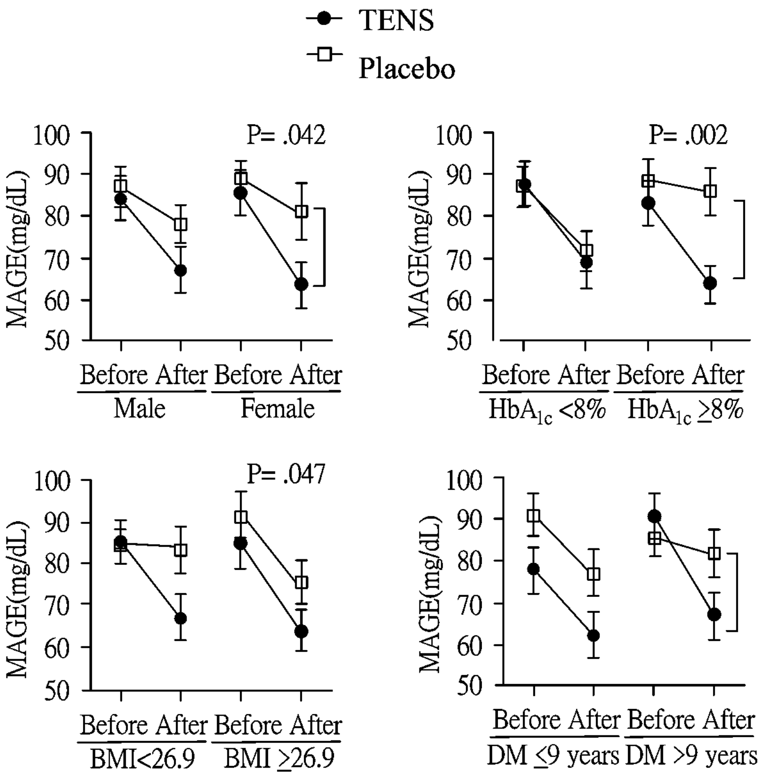
FIG. 3 is a graph of the mean amplitude of glycemic excursion (MAGE) of diabetic patients in different groups after using the electrical stimulation system in one embodiment of the present invention.

Next, the efficacy of the electrical stimulation system of the present invention in different subject groups was further studied. As shown in FIG. 3, after the TENS group and the placebo group were treated with the electrical stimulation system of the present invention, the data of MAGE especially in the subjects of the women group (P=0.042), HbA1c≥8.0% group (P=0.002), and BMI<26.9 kg/m2 group (P=0.047), the decline results of the data have statistically significant differences. It can be seen that the electrical stimulation system of the present invention can reduce the MAGE value of diabetic patients and has a remarkable efficacy of stabilizing blood glucose fluctuations.

Embodiment 2

[Reducing Inflammation]

Figure 4:
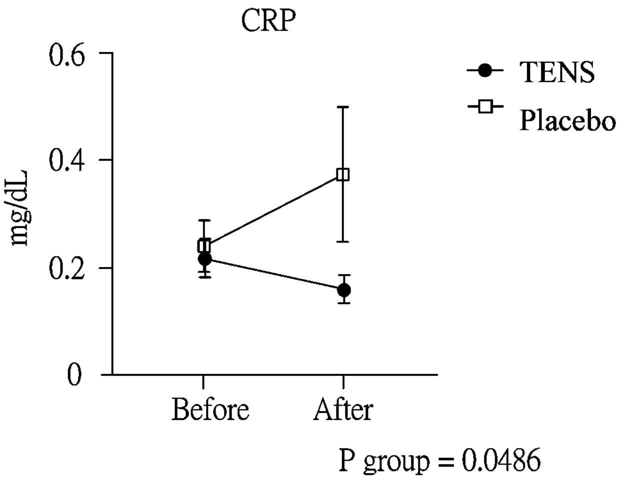
FIG. 4 is a graph of the inflammatory factor C-reactive protein (CRP) of the diabetic patients after applying the electrical stimulation system in one embodiment of the present invention.
Figure 5:
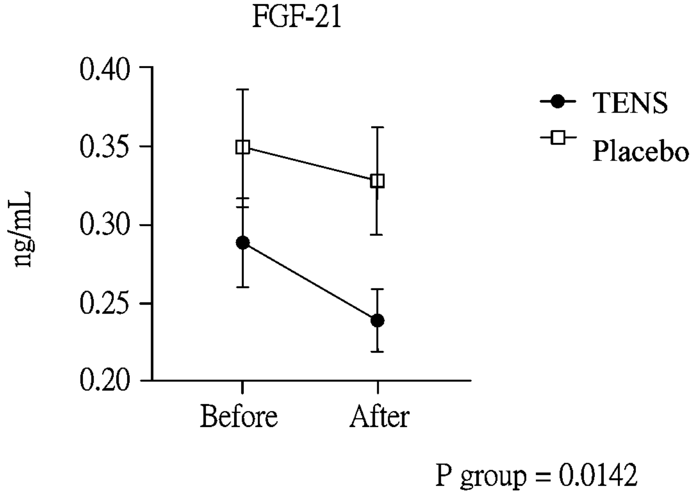
FIG. 5 is a graph of the inflammatory factor fibroblast growth factor 21 (FGF-21) of the diabetic patients after applying the electrical stimulation system in one embodiment of the present invention.

Next, the experiment analyzes whether there were differences in the inflammatory factors expressed in the blood samples after the subjects received the electrical stimulation system of the present invention for 20 weeks. Please refer to FIG. 4 to FIG. 5 and Table 1 for the results.

It showed that after the electrical stimulation treatment, the C-reactive protein (CRP) protein level measured from the TENS group decreased from 0.22 at the baseline state to 0.16, the placebo group increased from 0.24 at the baseline state to 0.38, and the fibroblast growth factor 21 (FGF-21) protein decreased from 0.29 at the baseline to 0.24, and in the placebo group, the FGF-21 protein decreased from 0.35 at the baseline to 0.32. The CRP and FGF-21 levels from week 0 to week 20 in the TENS group significantly decreased compared to the placebo group. From the data of the reduction of CRP and FGF-21 protein expression, it was found that the electrical stimulation system of the present invention can reduce the inflammation and potentially reduce fibrosis by reducing inflammatory cytokines in diabetic patients, thereby preventing the complications of diabetes.

In the embodiment of the present invention, as shown in Table 1, the results showed that after 20 weeks of electrical stimulation treatment, the glycosylated hemoglobin (HbA1c) of the TENS group decreased from 8.1 at the baseline to 7.9, and the HbA1c of the placebo group decreased from 8.1 at the baseline to 7.8, it can be realized that the expression level of HbA1c has no significant change in the TENS group and the placebo group. Thus the efficacy of stabilizing blood glucose fluctuations or reducing inflammation after using the electrical stimulation system was independent of HbA1c.

In summary, the electrical stimulation system and its application method of the present invention can effectively achieve the effects of stabilizing blood glucose fluctuations and reducing glycemic variability (GV), as well as the special effect of reducing inflammation that has not been found in the prior art.

Although the present invention has been described in considerable detail regarding certain embodiments thereof, other embodiments are possible. Therefore, the spirit and scope of the appended claims should not be limited to the description of the embodiments contained herein.

What is claimed is:

1. An electrical stimulation system, comprising:

an electrical stimulation generator used to generate an electric pulse combination, wherein a frequency of the electric pulse combination ranging from 1 to 20,000 Hz, and comprises a first frequency group, a second frequency group, and a third frequency group, wherein the first frequency group, the second frequency group, and the third frequency group are respectively composed of multiple single-phase pulse groups, wherein each single-phase pulse group has a duty cycle greater than or equal to 50% and a waveform that is a square wave;

at least one electrode structure electrically connected to the electrical stimulation generator and having a contact surface applied to the skin of an individual to deliver the electric pulse combination;

wherein the electric pulse combination is outputted in sequence from the first frequency group to the third frequency group, wherein the first frequency group ranges from 10 to 20,000 Hz, the second frequency group ranges from 1 to 30 Hz, and the third frequency group ranges from 5 to 30 Hz, the output time of the first frequency group is between 2300 and 2350 seconds, the output time of the second frequency group is between 900 and 1000 seconds, and the output time of the third frequency group is between 320 and 400 seconds.

2. The electrical stimulation system of claim 1, wherein the output time of the electric pulse combination is between 3520 and 3750 seconds.

3. The electrical stimulation system of claim 1, wherein the electric pulse combination has a potential difference, which is less than 10 Vpp.

4. The electrical stimulation system of claim 1, wherein the electrode structure contacts the abdominal skin of the individual.

5. The electrical stimulation system of claim 1, wherein the electrical stimulation system is capable of improving symptoms of diabetes, which includes stabilizing blood glucose fluctuations or reducing inflammation.

6. The electrical stimulation system of claim 5, wherein stabilizing blood glucose fluctuations refers to reducing glycemic variability (GV).

7. The electrical stimulation system of claim 5, wherein reducing inflammation refers to decreasing the protein expression of C-reactive protein (CRP) and fibroblast growth factor 21 (FGF-21).

8. A method using the electrical stimulation system of claim 1.

* * * * *